(12) United States Patent
Xu et al.

(10) Patent No.: US 11,099,146 B1
(45) Date of Patent: Aug. 24, 2021

(54) COAL MINE ADVANCED DETECTION METHOD FOR HEADING MACHINE

(71) Applicant: CHINA UNIVERSITY OF MINING AND TECHNOLOGY, Jiangsu (CN)

(72) Inventors: Shaoyi Xu, Jiangsu (CN); Zhencai Zhu, Jiangsu (CN); Wei Li, Jiangsu (CN); Yanjing Sun, Jiangsu (CN); Fangfang Xing, Jiangsu (CN); Hongyu Xue, Jiangsu (CN); Qiang Peng, Jiangsu (CN); Feng Dong, Jiangsu (CN); Guang Chen, Jiangsu (CN)

(73) Assignee: CHINA UNIVERSITY OF MINING AND TECHNOLOGY, Jiangsu (CN)

( * ) Notice: Subject to any disclaimer, the term of this patent is extended or adjusted under 35 U.S.C. 154(b) by 0 days.

(21) Appl. No.: 17/264,412

(22) PCT Filed: Mar. 13, 2020

(86) PCT No.: PCT/CN2020/079258
§ 371 (c)(1),
(2) Date: Jan. 29, 2021

(51) Int. Cl.
*G01N 27/12* (2006.01)
*G01N 33/24* (2006.01)
(Continued)

(52) U.S. Cl.
CPC ........... *G01N 27/121* (2013.01); *E21C 39/00* (2013.01); *G01N 21/41* (2013.01); *G01N 27/125* (2013.01);
(Continued)

(58) Field of Classification Search
CPC .. G01N 27/048; G01N 27/121; G01N 33/246; E21C 39/00
See application file for complete search history.

(56) References Cited

U.S. PATENT DOCUMENTS

| 5,182,449 | A |  | 1/1993 | Johnson et al. |
| 2009/0058422 | A1 | * | 3/2009 | Tenghamn ............. G01V 3/083 324/337 |

(Continued)

FOREIGN PATENT DOCUMENTS

| CN | 101251427 A | 8/2008 |
| CN | 201100865 Y | 8/2008 |

(Continued)

OTHER PUBLICATIONS

Written Opinion issued in corresponding International Application No. PCT/CN2020/079258; dated Sep. 21, 2020; 6 pgs.
(Continued)

*Primary Examiner* — Paul M. West
(74) *Attorney, Agent, or Firm* — Hauptman Ham, LLP

(57) ABSTRACT

When the heading machine tunnels, a current generated by a current excitation source enters a coal seam through a movable cutting pick to form a stray current. The stray current collected by a backflow net returns to a negative electrode of a power supply through a transition resistor. When information such as the water content of the coal seam changes, the stray current and a potential difference across the transition resistor also accordingly change, and the coal seam water content information is converted into an electric signal. When the potential difference across the transition resistor is applied to two ends of a piezoelectric ceramic, the piezoelectric ceramic extends or compresses, and the electric signal is converted into a strain signal. A sensing optical fiber converts the strain signal into an optical signal detectable by a photoelectric detector. The optical signal is analyzed to obtain the coal seam water content information.

6 Claims, 1 Drawing Sheet

(51) Int. Cl.
*E21C 39/00* (2006.01)
*G01N 21/41* (2006.01)

(52) U.S. Cl.
CPC ... *G01N 33/246* (2013.01); *G01N 2201/0636* (2013.01)

(56) References Cited

U.S. PATENT DOCUMENTS

2017/0160422 A1\* 6/2017 Donderici ................ G01V 3/28
2018/0283168 A1\* 10/2018 Ranjan .................... E21B 47/00

FOREIGN PATENT DOCUMENTS

| CN | 101446600 A | 6/2009 |
| CN | 102636197 A | 8/2012 |
| CN | 202649483 U | 1/2013 |
| CN | 104390694 A | 3/2015 |
| CN | 105806592 A | 7/2016 |
| CN | 207866878 U | 9/2018 |

OTHER PUBLICATIONS

International Search Report issued in corresponding International Application No. PCT/CN2020/079258; dated Sep. 21, 2020; 5 pgs.

\* cited by examiner

COAL MINE ADVANCED DETECTION METHOD FOR HEADING MACHINE

RELATED APPLICATIONS

The present application is a U.S. National Phase of International Application Number PCT/CN2020/079258, filed Mar. 13, 2020, and claims the priority of Chinese Application No. 201911301527.7, filed Dec. 17, 2019.

FIELD OF THE INVENTION

The present invention relates to the technical field of coal mine detection, more particularly relates to a coal mine advanced detection method for a heading machine.

DESCRIPTION OF RELATED ART

With the continuous improvement of safety requirements of coal mining, it is very important to obtain information such as a coal seam structure in advance during coal mining. The special geology such as a water-bearing structure, a fault and a fractured zone in the coal seam easily causes coal mine accidents such as collapse and water permeability during mining. Therefore, there is a need for safe and reliable advanced detection equipment and methods to predict the coal seam information of the coal mine and avoid casualties and equipment damage.

When the structure or water content in the coal seam is abnormal, the resistivity of the coal seam also accordingly changes. The condition of the coal seam can be effectively known through the stray current passing through the coal seam. Piezoelectric ceramics and optical fiber sensing, having strong anti-electromagnetic interference capability and high sensitivity, can fast and accurately transmit information, providing a guarantee for safe mining of the coal mine.

Traditional advanced detection methods mainly include geological exploration and physical exploration. The geological exploration is labor-consuming. Technologies such as acoustic emission and geological radar used in physical exploration easily suffer from electromagnetic interference, and the cost is higher.

SUMMARY OF THE INVENTION

Technical Problem

An objective of the present invention is to provide a coal mine advanced detection method for a heading machine. The advanced detection of a coal mine can be realized, and additionally, the cost is lower.

Technical Solution

In order to achieve the above objective, the present invention adopts the following technical solution: According to the coal mine advanced detection method for the heading machine, a used detection device includes an optical path module and a circuit module. The optical path module includes a broadband light source, a circulator, a sensing optical fiber, a reflector and a photoelectric detector. The circuit module includes a current excitation source, a piezoelectric ceramic, a transition resistor, a backflow net and a movable cutting pick. The broadband light source is connected with a first port of the circulator. A second port of the circulator is connected with the reflector through the sensing optical fiber. A third port of the circulator is connected with the photoelectric detector. A negative electrode of the current excitation source is separately connected with a first electrode of the piezoelectric ceramic and a first interface of the transition resistor. A positive electrode of the current excitation source is connected with the movable cutting pick. The piezoelectric ceramic is formed by overlapping a first piezoelectric ceramic piece and a second piezoelectric ceramic piece in the same polarization direction. The sensing optical fiber passes through a gap between the first piezoelectric ceramic piece and the second piezoelectric ceramic piece, and is tightly pressed. A second electrode of the piezoelectric ceramic is separately connected with a second interface of the transition resistor and the backflow net. The broadband light source, the circulator and the photoelectric detector are encapsulated in a main control chamber of the heading machine together. The sensing optical fiber is connected to a cutting part of the heading machine from the main control chamber. The current excitation source is positioned in the main control chamber of the heading machine. The piezoelectric ceramic is fixedly disposed in the cutting part of the heading machine through a support frame. The backflow net is distributed on the inner wall of the cutting part. The movable cutting pick is fixed to a head part of the cutting part through tensioned screw bolts. An insulation gasket is disposed between the tensioned screw bolts and the cutting part.

The detection method includes the following steps:

A, enabling output light of the broadband light source to enter the circulator from the first port, forming linearly polarized light in a transmission light path from the first port to the second port, and outputting the linearly polarized light from the second port; enabling the linearly polarized light output from the second port to reach the reflector through the sensing optical fiber, and to return to the sensing optical fiber after being reflected by the reflector; enabling the linearly polarized light in the sensing optical fiber to enter the circulator through the second port, and outputting the linearly polarized light from the third port; enabling the linearly polarized light output from the third port to enter the photoelectric detector; and obtaining phase information of light after photoelectric conversion;

B, when the heading machine tunnels, enabling a current output by the current excitation source from the positive electrode to enter a coal seam through the movable cutting pick to form a stray current; enabling the stray current collected by the backflow net through a wall of the cutting part to return to the negative electrode of the current excitation source through the transition resistor; generating a certain voltage difference carrying coal seam water content information across the transition resistor;

C, enabling the voltage across the transition resistor to act on the two electrodes of the piezoelectric ceramic to form an electric field, so as to deform the first piezoelectric ceramic piece and the second piezoelectric ceramic piece under the effect of the electric field, and at the same time, extrude the sensing optical fiber positioned between the first piezoelectric ceramic piece and the second piezoelectric ceramic piece; and D, after the sensing optical fiber is extruded, enabling a phase difference of the linearly polarized light to change under the effect of stress, finally obtaining the coal seam water content information in the photoelectric detector through photoelectric conversion, and realizing advanced detection.

Preferably, the transmission light path between the first port and the second port of the circulator is unidirectional, and the transmission light path has an extinction ratio of being ≥32 dB. A transmission light path between the second port and the third port of the circulator is unidirectional, and the transmission light path has an extinction ratio of being ≥32 dB.

Preferably, the part of the sensing optical fiber extruded by the piezoelectric ceramic is a Panda polarization-holding optical fiber, and other parts are rotating high birefringence optical fibers insensitive to vibration.

Preferably, the current excitation source is a direct current constant voltage power supply having a positive electrode potential of 30 V and a negative electrode potential of 0 V.

Preferably, the piezoelectric ceramic is a polarized barium titanate piezoelectric ceramic, a polarization direction is a direction vertical to a combination surface of the first piezoelectric ceramic piece and the second piezoelectric ceramic piece. Additionally, a certain prestress is applied to two end surfaces of the first electrode and the second electrode of the piezoelectric ceramic.

Preferably, the transition resistor has a resistance value of being ≥500 Ohm.

Advantageous Effect

Compared with the prior art, the present invention has the following advantageous effects:

The present invention forms a coal mine advanced detection device for a heading machine by combining optical devices with electric devices, and realizes the advanced detection of the coal mine. By detecting the stray current in the coal seam, information such as the water content of the coal seam can be obtained. The electricity and strain conversion is realized by using the inverse piezoelectric effect of the piezoelectric ceramic. Then, the conversion of the strain and the optical phase information is realized by using the sensitivity of the optical fiber sensing to the stress. The present invention has the advantages of strong anti-electromagnetic interference capability and simple structure.

In the figures, 1 denotes a broadband light source; 2 denotes an optical fiber circulator; 21 denotes a first port; 22 denotes a second port; 23 denotes a third port; 3 denotes a sensing optical fiber; 4 denotes a reflector; 5 denotes a photoelectric detector; 6 denotes a current excitation source; 61 denotes a negative electrode; 62 denotes a positive electrode; 7 denotes a piezoelectric ceramic; 71 denotes a first piezoelectric ceramic piece; 72 denotes a second piezoelectric ceramic piece; 711 denotes a first electrode; 712 denotes a second electrode; 8 denotes a transition resistor; 81 denotes a first interface; 82 denotes a second interface; 9 denotes a backflow net; 10 denotes a movable cutting pick; and 11 denotes a cutting part.

DETAILED DESCRIPTION OF THE INVENTION

The present invention will be described in detail below with reference to the accompanying drawings and specific embodiments.

The present invention provides a coal mine advanced detection method for a heading machine. A used detection device includes an optical path module and a circuit module.

Figure 1:
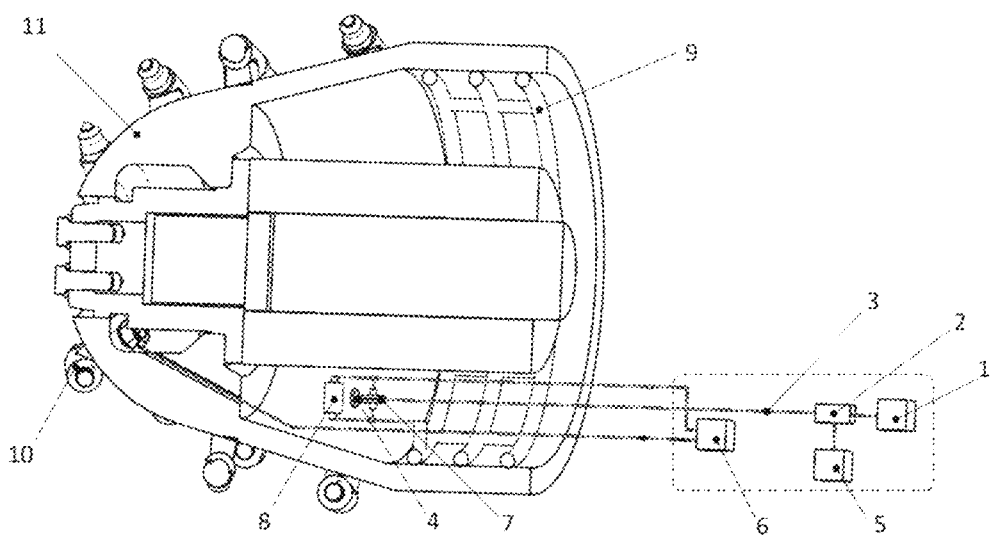
FIG. 1 is a schematic diagram of integral arrangement of a detection device used by the present invention.
Figure 2:
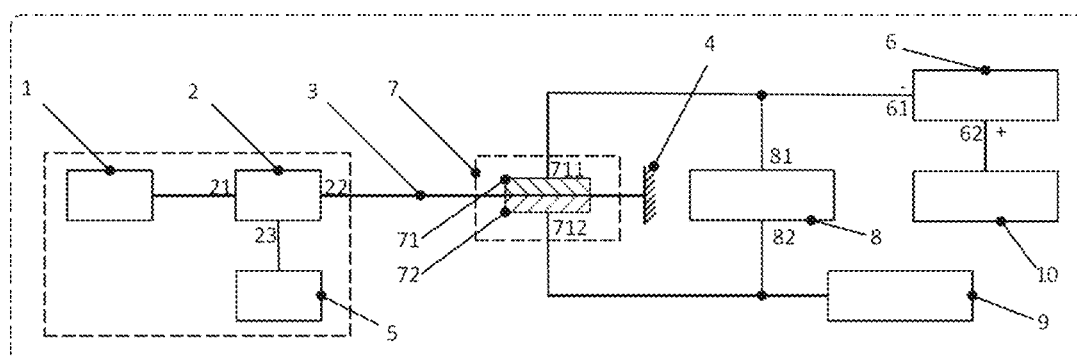
FIG. 2 is a connection principle diagram of the detection device used by the present invention.

As shown in FIG. 1 and FIG. 2, the optical path module includes a broadband light source 1, a circulator 2, a sensing optical fiber 3, a reflector 4 and a photoelectric detector 5. The circuit module includes a current excitation source 6, a piezoelectric ceramic 7, a transition resistor 8, a backflow net 9 and a movable cutting pick 10.

The broadband light source 1 is connected with a first port 21 of the circulator 2. A second port 22 of the circulator 2 is connected with the reflector 4 through the sensing optical fiber 3. A third port 23 of the circulator 2 is connected with the photoelectric detector 5. A negative electrode 61 of the current excitation source 6 is separately connected with a first electrode 711 of the piezoelectric ceramic 7 and a first interface 81 of the transition resistor 8. A positive electrode 62 of the current excitation source 6 is connected with the movable cutting pick 10. The piezoelectric ceramic 7 is formed by overlapping a first piezoelectric ceramic piece 71 and a second piezoelectric ceramic piece 72 in the same polarization direction. The sensing optical fiber 3 passes through a gap between the piezoelectric ceramic piece 71 and the second piezoelectric ceramic piece 72, and is tightly pressed. A second electrode 712 of the piezoelectric ceramic 7 is separately connected with a second interface 82 of the transition resistor 8 and the backflow net 9.

The broadband light source 1, the circulator 2 and the photoelectric detector 5 are encapsulated in a main control chamber of the heading machine together. A transmission light path between the first port 21 and the second port 22 of the circulator 2 is unidirectional, and the transmission light path has an extinction ratio of being ≥32 dB. A transmission light path between the second port 22 and the third port 23 of the circulator 2 is unidirectional, and the transmission light path has an extinction ratio of being ≥32 dB.

The sensing optical fiber 3 is connected to the cutting part 11 of the heading machine from the main control chamber. The part of the sensing optical fiber 3 extruded by the piezoelectric ceramic 7 is a Panda polarization-holding optical fiber, and other parts are rotating high birefringence optical fibers insensitive to vibration.

The reflector 4 is fixedly disposed in the cutting part 11 of the heading machine through a support frame.

The current excitation source 6 is positioned in the main control chamber of the heading machine. The current excitation source 6 is a direct current constant voltage power supply having a positive electrode potential of 30 V and a negative electrode potential of 0 V.

The piezoelectric ceramic 7 is fixedly disposed in the cutting part 11 of the heading machine through a support frame. The piezoelectric ceramic 7 is a polarized barium titanate piezoelectric ceramic, and a polarization direction is a direction vertical to a combination surface of the first piezoelectric ceramic piece 71 and the second piezoelectric ceramic piece 72. Additionally, a certain prestress is applied to two end surfaces of the first electrode 711 and the second electrode 712 of the piezoelectric ceramic 7.

The transition resistor 8 is disposed inside the cutting part 11 of the heading machine, and the transition resistor 8 has a resistance value of being ≥500 Ohm.

The backflow net 9 is distributed on an inner wall of the cutting part 11, and is connected with the second electrode 712 of the piezoelectric ceramic 7 through a copper conductor.

The movable cutting pick 10 is positioned at the head part of the cutting part 11, and is fixed onto the cutting part 11 through four tensioned screw bolts. An insulation gasket is disposed between the tensioned screw bolts and the cutting part 11. For example, the movable cutting pick 10 and the cutting part 11 are isolated by an insulation rubber pad. The movable cutting pick 10 is connected with the positive electrode of the current excitation source 6 through a conductor.

The detection method includes the following steps:

A: Output light of the broadband light source 1 enters the circulator 2 from the first port 21. Linearly polarized light is formed in the transmission light path from the first port 21 to the second port 22, and is output from the second port 22. The linearly polarized light output from the second port 22 reaches the reflector 4 through the sensing optical fiber 3, and returns to the sensing optical fiber 3 after being reflected by the reflector 4. The linearly polarized light in the sensing optical fiber 3 enters the circulator 2 through the second port 22, and is output from the third port 23. The linearly polarized light output from the third port 23 enters the photoelectric detector 5, and phase information of light is obtained after photoelectric conversion.

B: When the heading machine tunnels, a current output by the current excitation source 6 from the positive electrode 62 enters a coal seam through the movable cutting pick 10 to form a stray current. The stray current collected by the backflow net 9 through a side wall of the cutting part 11 returns to the negative electrode 61 of the current excitation source 6 through the transition resistor 8. A certain voltage difference is generated across the transition resistor 8, and the voltage difference carries the coal seam water content information. Because the resistivity of the coal seam is related to features such as the water content of the coal seam, when information such as the water content of the coal seam changes, the stray current and a potential difference across the transition resistor also accordingly change, and the coal seam water content information is converted into an electric signal.

C: The voltage across the transition resistor 8 acts on the two electrodes of the piezoelectric ceramic 7 to form an electric field, so as to deform the first piezoelectric ceramic piece 71 and the second piezoelectric ceramic piece 72 under the effect of the electric field, and at the same time, extrude the sensing optical fiber 3 positioned between the first piezoelectric ceramic piece 71 and the second piezoelectric ceramic piece 72. When the potential difference across the transition resistor 8 is applied to two ends of the piezoelectric ceramic 7, the piezoelectric ceramic 7 extends or compresses, and the electric signal is converted into a strain signal.

D: After the sensing optical fiber 3 is extruded, a phase difference of the linearly polarized light changes under the effect of stress. The phase change is as follows:

$$\Delta\varphi = \frac{2\pi}{\lambda} \cdot L \cdot \frac{n^3 \cdot P_e \cdot P}{2E} \cdot \Delta\varphi$$

is phase change. $\lambda$, is the light wavelength. L is a length of the optical fiber. n is a fiber core refractive index of the sensing optical fiber. $P_e$ is a photoelastic coefficient. P is stress. E is Young modulus. Finally, the coal seam water content information is obtained in the photoelectric detector 5 through photoelectric conversion. The sensing optical fiber 3 is extruded by the piezoelectric ceramic 7, and converts the strain signal into the optical signal. The optical signal reaches the photoelectric detector 5 through the sensing optical fiber 3. The demodulated optical signal is analyzed to obtain the coal seam water content information, so that the advanced detection is realized.

The foregoing descriptions are merely preferred embodiments of the present invention, and are not intended to limit the present invention in any form. All other embodiments obtained by a person of ordinary skill in the art based on the embodiments of the present invention without creative efforts shall fall within the protection scope of the present invention. Any simple alteration or equivalent change made to the above embodiments according to the technical essence of the present invention shall fall within the scope of the technical solutions of the present invention.

What is claimed is:

1. A coal mine advanced detection method for a heading machine, wherein a used detection device comprises an optical path module and a circuit module, the optical path module comprises a broadband light source, a circulator, a sensing optical fiber, a reflector and a photoelectric detector, the circuit module comprises a current excitation source, a piezoelectric ceramic, a transition resistor, a backflow net and a movable cutting pick, the broadband light source is connected with a first port of the circulator, a second port of the circulator is connected with the reflector through the sensing optical fiber, a third port of the circulator is connected with the photoelectric detector, a negative electrode of the current excitation source is separately connected with a first electrode of the piezoelectric ceramic and a first interface of the transition resistor, a positive electrode of the current excitation source is connected with the movable cutting pick, the piezoelectric ceramic is formed by overlapping a first piezoelectric ceramic piece and a second piezoelectric ceramic piece in the same polarization direction, the sensing optical fiber passes through a gap between the first piezoelectric ceramic piece and the second piezoelectric ceramic piece, and is tightly pressed, a second electrode of the piezoelectric ceramic is separately connected with a second interface of the transition resistor and the backflow net, the broadband light source, the circulator and the photoelectric detector are encapsulated in a main control chamber of the heading machine together, the sensing optical fiber is connected to a cutting part of the heading machine from the main control chamber, the current excitation source is positioned in the main control chamber of the heading machine, the piezoelectric ceramic is fixedly disposed in the cutting part of the heading machine through a support frame, the backflow net is distributed on the inner wall of the cutting part, the movable cutting pick is fixed to a head part of the cutting part through tensioned screw bolts, and an insulation gasket is disposed between the tensioned screw bolts and the cutting part; and the detection method comprises the following steps:

A, enabling output light of the broadband light source to enter the circulator from the first port, forming linearly polarized light in a transmission light path from the first port to the second port, and outputting the linearly polarized light from the second port; enabling the linearly polarized light output from the second port to reach the reflector through the sensing optical fiber, and to return to the sensing optical fiber after being reflected by the reflector; enabling the linearly polarized light in the sensing optical fiber to enter the circulator from the second port, and outputting the linearly polarized light from the third port; enabling the linearly polarized light output from the third port to enter the photoelectric detector; and obtaining phase information of light after photoelectric conversion;

B, when the heading machine tunnels, enabling a current output by the current excitation source from the positive electrode to enter a coal seam through the movable cutting pick to form a stray current; enabling the stray current collected by the backflow net through a side wall of the cutting part to return to the negative electrode of the current excitation source through the transition resistor; generating a certain voltage difference carrying coal seam water content information across the transition resistor;

C, enabling the voltage across the transition resistor to apply on the two electrodes of the piezoelectric ceramic to form an electric field, so as to deform the first piezoelectric ceramic piece and the second piezoelectric ceramic piece under the effect of the electric field, and at the same time, extrude the sensing optical fiber positioned between the first piezoelectric ceramic piece and the second piezoelectric ceramic piece; and D, after the sensing optical fiber is extruded, enabling a phase difference of the linearly polarized light to change under the effect of stress, finally obtaining the coal seam water content information in the photoelectric detector through photoelectric conversion, and realizing advanced detection.

2. The coal mine advanced detection method for the heading machine according to claim 1, wherein the transmission light path between the first port and the second port of the circulator is unidirectional, and the transmission light path has an extinction ratio of being ≥32 dB; and a transmission light path between the second port and the third port of the circulator is unidirectional, and the transmission light path has an extinction ratio of being ≥32 dB.

3. The coal mine advanced detection method for the heading machine according to claim 1, wherein the part of the sensing optical fiber extruded by the piezoelectric ceramic is a Panda polarization-holding optical fiber, and other parts are rotating high birefringence optical fibers insensitive to vibration.

4. The coal mine advanced detection method for the heading machine according to claim 1, wherein the current excitation source is a direct current constant voltage power supply having a positive electrode potential of 30 V and a negative electrode potential of 0 V.

5. The coal mine advanced detection method for the heading machine according to claim 1, wherein the piezoelectric ceramic is a polarized barium titanate piezoelectric ceramic, a polarization direction is a direction vertical to a combination surface of the first piezoelectric ceramic piece and the second piezoelectric ceramic piece, a certain prestress is applied to two end surfaces of the first electrode and the second electrode of the piezoelectric ceramic.

6. The coal mine advanced detection method for the heading machine according to claim 1, wherein the transition resistor has a resistance value of being ≥500 Ohm.

* * * * *

UNITED STATES PATENT AND TRADEMARK OFFICE
CERTIFICATE OF CORRECTION

PATENT NO. : 11,099,146 B1
APPLICATION NO. : 17/264412
DATED : August 24, 2021
INVENTOR(S) : Shaoyi Xu et al.

Page 1 of 1

It is certified that error appears in the above-identified patent and that said Letters Patent is hereby corrected as shown below:

On the Title Page

Insert item (30) Foreign Application Priority Data as follows:
(30)   Foreign Application Priority Data
Dec. 17, 2019   (CN) ..................... 201911301527.7

Signed and Sealed this
Nineteenth Day of October, 2021

Drew Hirshfeld
*Performing the Functions and Duties of the*
*Under Secretary of Commerce for Intellectual Property and*
*Director of the United States Patent and Trademark Office*